US008247187B2

(12) United States Patent
Jucker et al.

(10) Patent No.: US 8,247,187 B2
(45) Date of Patent: Aug. 21, 2012

(54) METHOD FOR DETECTING PATHOGENS

(75) Inventors: Markus Jucker, Renton, WA (US); Philip T. Feldsine, Mercer Island, WA (US); Andrew Lienau, Seattle, WA (US)

(73) Assignee: BioControl Systems, Inc., Bellevue, WA (US)

( * ) Notice: Subject to any disclaimer, the term of this patent is extended or adjusted under 35 U.S.C. 154(b) by 8 days.

(21) Appl. No.: 11/838,479

(22) Filed: Aug. 14, 2007

(65) Prior Publication Data

US 2008/0070262 A1   Mar. 20, 2008

Related U.S. Application Data

(60) Provisional application No. 60/837,469, filed on Aug. 14, 2006.

(51) Int. Cl.
*G01N 33/569* (2006.01)
(52) U.S. Cl. .................... 435/7.3; 435/7.2; 435/7.32
(58) Field of Classification Search ................ None
See application file for complete search history.

(56) References Cited

U.S. PATENT DOCUMENTS

| | | | | |
|---|---|---|---|---|
| 4,900,669 A * | 2/1990 | Hatch et al. | ................... | 435/108 |
| 5,100,801 A * | 3/1992 | Ward et al. | ................. | 435/304.2 |
| 5,188,946 A * | 2/1993 | Ward et al. | .................... | 435/6.11 |
| 5,415,997 A * | 5/1995 | Atrache et al. | ............... | 435/7.35 |
| 5,658,747 A | 8/1997 | Feldsine et al. | | |
| 6,004,766 A * | 12/1999 | Atrache et al. | ............... | 435/7.94 |
| 6,087,105 A * | 7/2000 | Chan et al. | ......................... | 435/6 |
| 6,342,352 B1 | 1/2002 | Schuch et al. | .................... | 435/6 |
| 6,872,549 B2 * | 3/2005 | Van Ness et al. | ............ | 435/69.1 |
| 7,232,569 B2 * | 6/2007 | Frey et al. | .................. | 424/185.1 |
| 7,244,588 B2 * | 7/2007 | Tomono et al. | ............... | 435/69.1 |
| 7,351,861 B2 * | 4/2008 | Kauppi et al. | ................. | 564/152 |
| 7,560,246 B2 * | 7/2009 | Townsend | ....................... | 435/34 |
| 2002/0058298 A1 * | 5/2002 | Townsend | ....................... | 435/34 |
| 2002/0164574 A1 * | 11/2002 | Tanzer et al. | ..................... | 435/4 |
| 2003/0017524 A1 * | 1/2003 | Hall et al. | ........................ | 435/29 |
| 2003/0059839 A1 | 3/2003 | Obiso et al. | | |
| 2003/0108997 A1 * | 6/2003 | Mahr et al. | .................... | 435/69.1 |
| 2003/0211579 A1 * | 11/2003 | Van Ness et al. | ............ | 435/69.1 |
| 2004/0121445 A1 * | 6/2004 | Marino et al. | ............. | 435/252.3 |
| 2005/0058662 A1 * | 3/2005 | Frey et al. | ................... | 424/190.1 |
| 2005/0065737 A1 * | 3/2005 | Benson | ........................... | 702/20 |
| 2006/0134724 A1 * | 6/2006 | Kauppi et al. | ................. | 435/2 |
| 2006/0148033 A1 * | 7/2006 | Tomono et al. | ............... | 435/69.1 |
| 2007/0020720 A1 * | 1/2007 | Colin et al. | ...................... | 435/34 |
| 2007/0065906 A1 * | 3/2007 | Koyanagi et al. | ............ | 435/69.1 |
| 2007/0178117 A1 * | 8/2007 | Marconi et al. | ............ | 424/190.1 |
| 2008/0070262 A1 * | 3/2008 | Jucker et al. | .................... | 435/7.3 |

FOREIGN PATENT DOCUMENTS

| | | | |
|---|---|---|---|
| AU | 200229229 | * | 5/2002 |
| EP | 1 059 358 A1 | | 12/2000 |
| WO | 95/30903 A1 | | 11/1995 |
| WO | 2004/092401 | * | 11/2004 |

OTHER PUBLICATIONS

Grundling, Angelika et al, PNAS, Aug. 17, 2004, vol. 101, No. 33, pp. 12318-12323, Listeria monocytogenes regulates flagellar motility gene expression through MogR, a transcriptional repressor required for virulence.*
Shen, A et al, PLoS Pathogens, Apr. 2006, vol. 2(4), pp. 0282-0294, The MogR transcriptional Repressor Regulates Nonhierarchal Expression of Flagellar Motility Genes and Virulence in Listeria monocytogenes.*
Leimeister-Wachter, M et al, Journal of Bacteriology, vol. 174(3), Feb. 1992, pp. 947-952, The expression of Virulence Genes in Listeria monocytogenes is thermoregulated.*
Wassenaar, Trudy M. et al, Infection and Immunity, vol. 62(9), pp. 3901-3906, Sep. 1994, Differential Flagellin Expression in a flaA flaB+ Mutant of Campylobacter jejuni.*
Zhao, Chun et al, Molecular and Cellular Biology, Feb. 1998, vol. 18(2), pp. 1013-1022, Temperature-Induced Expresion of Yeast FKS2 Is under the Dual Control of Protein Kinase C and Calcineurin.*
Falconi, M et al, EMBO journal , vol. 17(23), pp. 7033-7043, 1998, Thermoregulation of Shigella and *Escherichia coli* EIEC pathogenicity. A temperature-dependent structural transition of DNA modulates accessibility of virF promoter to transcriptional repressor H-NS.*
Yourng, Briana M et al, Journal of Bacteriology, vol. 184(5), pp. 1324-1334, Mar. 2002, YpIA is exported by the Ysc, Ysa and Flagellar Type III Secretion Systems of *Yersinia enterocolitica*.*
Heuner, K et al, Infection and Immunity, vol. 63(7), pates 2499-2507, Jul. 1995, Cloning and Genetic Characterization of the Flagellum Subunit Gene (flaA) of *Legionella pneumophila* Serogroup I.*
Schofield, David A et al, Applied and Environmental Microbiology, Jun. 2003, vol. 69(6), pp. 3385-3392, Development of a Thermally Regulated Broad Spectrum Promoter system for use in pathogenic Gram Positive Species.*
Segal, Gil et al, Journal of Bacteriology, Jun. 1996, vol. 178(12), pp. 3634-3640, Heat Shock Activation of the groESL Operon of *Agrobacterium tumefaciens* and the Regulatory Roles of the Inverted Repeat.*
Alm, Richard A. et al, Journal of Bacteriology, Jul. 1993, pp. 4448-4455, vol. 175 (14), The Campylobacter sigma-54 flaB Flagellin Promoter Is Subject to Environmental Regulation.*
Grundling, A et al, PNAS, Aug. 17, 2004, vol. 101(33), pp. 12318-12323.*
Williams, Norman E. et al, Molecular and Cellular Biology, Aug. 1985, vol. 5(8), pp. 1925-1932, Expression of Cell Surface immobilization antigen during serotype transformation in *Tetrahymena thermophila*.*
Coleman, Sherry A et al, Microbial Pathogenesis, vol. 34, 2003, pp. 179-186, Differential expresssion of the invasion-associated locus B (ialB) gene of *Bartonella bacilliformis* in response to environmental cues.*

(Continued)

*Primary Examiner* — Albert Navarro
*Assistant Examiner* — Ginny Portner

(57) ABSTRACT

The present invention relates generally to methods for detecting and identifying microorganisms and, more particularly, to methods for detecting microorganisms in a sample by incubating the sample at two temperatures to facilitate increased detection of the organism.

3 Claims, No Drawings

OTHER PUBLICATIONS

Grundling, A et al, 2004, reference of record.*

Garcia, Emilo et al, Journal of Bacteriology, May 1999, vol. 181(10), pp. 3114-3122, Molecular Characterization of KatY (Antigen 5), a thermoregulated Chromosomally encoded Catalase Peroxidase of Yersinia pestis.*

Fuerst, JA et al, Journal of General Microbiology, 11980, vol. 117, pp. 111-117, The effect of temperature on the formation of Sheathed flagella by *Pseudomonas stizolobii*.*

Bajard, S. et al, Int. J. Food Microbiology, vol. 29, 1996, pp. 201-211, The particular behavior of *Listeria monocytogenes* under sub-optinal conditions.*

Identification of Listeria species using *Microgen listeria*, Microbiology International,5111 Pegasus Ct., Suite H, Frederick, MD 21704 TN 12-15, pp. 1-2, Sep. 12, 2002.*

Peel, M et al, Journal of General Microbiology, 1988, vol. 134, pp. 2171-2178, Temperature-dependent expression of flagella of *Listeria monocytogenes* Studied by Electron Microscopy, SDS-PAGE and Western Blotting.*

Geng, T., et al., "Expression of Cellular Antigens of *Listeria monocytogenes* that React with monoclonal Antibodies C11E9 and EM-7G1 under acid-, salt- or temperature-induced stress environments," J. Appl. Microbiol., 95:762-772, 2003.

Gray, K., et al., "Specific Detection of Cytopathogenic *Listeria monocytogenes* using a Two-step Method of Immunoseparation and Cytotoxicity Analysis," J. Microbiol. Methods, 60:259-268, 2005.

Way, S., et al., "Characterization of Flagellin Expression and its Role in *Listeria monocytogenes* Infection and Immunity," Cellular Microbiology, 6(3):235-242, 2004.

Dons et al., "Cloning and characterization of a gene encoding flagellin of *Listeria monocytogenes*," Molecular Microbiology 6(20):2919-2929, 1992.

Peel et al., "Temperature-dependent Expression of Flagella of *Listeria monocytogenes* Studied by Electron Microscopy, SDS-PAGE and Western Blotting," Journal of General Microbiology 134:2171-2178, 1988.

* cited by examiner

METHOD FOR DETECTING PATHOGENS

CROSS-REFERENCE TO RELATED APPLICATION

This application claims the benefit under 35 U.S.C. §119(e) of U.S. Provisional Patent Application No. 60/837,469 filed Aug. 14, 2006, where this provisional application is incorporated herein by reference in its entirety.

BACKGROUND

1. Technical Field

The present invention relates generally to methods for detecting and identifying microorganisms and, more particularly, to methods for detecting microorganisms by enriching the microorganism in a sample in an incubator at one temperature which prevents production of a bacterial protein of interest (or other bacterial product) but which temperature allows for optimal growth of the microorganism. After a period of time, the whole sample or a portion of the sample is transferred and incubated at a different optimal temperature which allows expression of the protein previously inhibited. This dual temperature incubated sample is then tested by assaying the sample, or a portion thereof, with an assay suitable to detect the temperature regulated protein (or other bacterial product).

2. Description of the Related Art

Microbial diseases have long been a major health concern worldwide. Significant increase in the frequency and severity of outbreaks have occurred throughout the world. New pathogenic bacteria, such as *E. coli* 0157:H7, have been identified. Furthermore, previously recognized pathogenic genera have mutated to form drug resistant highly infectious strains such as *Salmonella typhimirium* DT 104. A key feature in the prevention of such diseases is early detection and early diagnosis. Epidemiologists must look for microbial contamination in the environment as well as in food products to find the effective disease prevention strategies.

One example is the outbreak in 1992 of Enterohemorrhagic *E. coli* (EHEC) in the Pacific Northwest of the United States due to contaminated ground beef. EHEC is a relatively "newly discovered" pathogen. EHEC was first isolated in 1975, and it was not until 1982 that *E. coli* 0157:H7 was associated with two food related outbreaks of hemorrhagic colitis in the United States. The reported incidence of *E. coli* 0157:H7 cases is increasing. Typically, *E. coli* strains are harmless commensals, but a few strains are pathogenic. EHEC is particularly virulent and can trigger deadly complications, including severe abdominal cramps and acute renal failure in children as well as cardiovascular and central nervous system problems.

As another example, *Salmonella* is the leading cause (more than 50%) of total bacterial foodborne disease outbreaks, according to the United States Centers for Disease Control (CDC) surveillance of foodborne diseases. More than 40,000 cases per year were reported to the CDC during the period 1988-1992. *Salmonella* can infect a broad variety of warm- and cold blooded animals, and can survive for long periods of time outside a host.

In a further example, *Salmonella typhimurium* DT 104 was first identified in the United Kingdom in the early 1990s. It is a highly adapted drug resistant strain of *Salmonella* known for its virulence. Resultingly, significant clinical interest has surrounded this serotype. *S. typhimurium* DT 104 contains core cell wall antigen epitopes that are highly conserved among the genus *Salmonella*.

*Listeria*, a genus of gram positive bacteria, is widely distributed in nature, having been isolated from soil, water, vegetation and many animal species. The detection frequency for *Listeria* in the agricultural environment appears to be increasing. For specific outbreaks of listeriosis, estimates place mortality at 30% to 40% of affected patients, however, little is known of the minimum infective dose. One particularly troublesome aspect of *Listeria* control in foods is that *Listeria* can grow at temperatures as low as $-0.4°$ C. and as high as $44°$ C. These factors all contribute to the increasing significance of *Listeria* as a food pathogen.

*Campylobacter jejuni* and coli have recently been identified as the lead causes of enteritis, especially from poultry sources. This has led to an increased need to discriminate these two species from several other *Campylobacter* species which are not human pathogens. This requires the differential selection of more specific cell wall membrane antigen epitopes.

The ability to monitor potential environmental and food sources of microbial contamination quickly and easily, but with very high specificity, would reduce the risk of human infection. Therefore, an analytical method which affords high specificity to detect microorganisms, including bacteria, yeasts, molds, fungi, parasites and viruses, that requires no special or technical equipment, can be performed in the field and does not require special skills would be useful. In the case of foodborne bacterial contamination, four of the major disease-related organisms are *Salmonella, Listeria*, EHEC and *Campylobacter*.

While there are a number of *Salmonella, Listeria*, and EHEC detection methods presently available, trained laboratory technicians and a minimum of 2-5 days are required to obtain test results by the standard cultural methods of analysis. New, more rapid methods are based on such techniques as enzyme linked immunoassay (EIA), DNA hybridization, immunodiffusion, or growth/metabolism measurements. While taking much less time than the cultural methods, these rapid tests still require skilled technical training, a functional laboratory, and specialized equipment. These tests generally take a total of two or more days, including considerable hands-on time. *Campylobacter* detection methodology to date is technically intensive requiring fastidious media and environmental conditions, in addition to well-trained analysts.

Another recent technology in the diagnostic field involves lateral flow immunoassays. Such tests have been developed for the detection of human chorionic gonadotropin (hCG), and applied to pregnancy testing. Typically, a monoclonal or polyclonal antibody is immobilized in a discrete band near the distal end of a solid carrier strip, called the detection zone. Another amount of antibody is labeled with a detection reagent such as an inorganic sol or dyed polystyrene particle. This labeled antibody is reversibly fixed near the proximal end of the carrier strip. Upon hydration of the proximal end with a sample fluid potentially containing the antigen, the antigen reacts with the labeled antibody and the complex passes through the zone of immobilized antibody, forming a sandwich upon reacting with the immobilized antibody. The capture of the chromogenic reagent-antigen complex causes the formation of a visible signal in the detection zone.

Two major challenges must be addressed to distinguish pathogenic bacteria, as opposed to distinguishing hormones or other soluble molecular targets. These challenges are the need to detect all of the strains of a pathogenic microorganism in the presence of numerous antigenically related organisms, with a low tolerance for false positive results and a very low, preferably zero, tolerance for false negatives. The second challenge is the physical size and heterogeneity of the microorganism itself. A typical clinical diagnostic test, such as a test for hCG in urine, is focused on detecting a single, small, unique entity (i.e., a hormone) in a well characterized matrix (e.g., urine). Furthermore, the structure of the analyte (hCG) is defined and uniform in size and composition.

Pathogen detection, for example, a test for *Salmonella*, must distinguish a particular pathogenic strain from non-pathogenic strains of similar microorganisms, such as *Citrobacter* spp. and *Enterobacter* spp. In contrast to the well-defined small size and structure of most hormones or marker proteins, microorganisms are very large, their surfaces are heterogeneous containing many distinct antigen epitopes that can undergo changes, such as the phase-switching of *Salmonella flagella*.

There is a need in the art for methodologies that will allow the simultaneous exposure of easily detected antigens while still allowing the microorganisms to multiply. Further, there is a need in the art to incorporate improved selectivity for highly conserved target antigen epitopes of specific species in a population of heterogeneous microorganisms in a variety of matrices. The present invention provides these and other, related advantages.

BRIEF SUMMARY

One aspect of the present invention provides a method for detecting a pathogen in a sample comprising, culturing the pathogen in the sample at a first temperature wherein the first temperature prevents production of at least one endogenous protein and wherein the first temperature allows for optimal growth of the pathogen; culturing the pathogen in the sample at a second temperature wherein the second temperature allows production of the at least one endogenous protein; and contacting the sample with a detection reagent that specifically binds to the at least one protein; thereby detecting the pathogen in the sample. In one embodiment, the pathogen comprises *Listeria*. In a further embodiment, the first temperature is about 37° C. In another embodiment, the second temperature is about 30° C. In one embodiment, the at least one endogenous protein comprises a flagellin protein.

DETAILED DESCRIPTION

Prior to setting forth the invention, it may be helpful to an understanding thereof to set forth definitions of certain terms that will be used hereinafter.

The term "antibody" as used herein includes polyclonal, monoclonal, humanized, chimeric, and anti-idiotypic antibodies, as well as fragments thereof such as F(ab')$_2$ and Fab fragments and other recombinantly produced binding partners. Further, the antibodies may be covalently linked to or recombinantly fused to an enzyme, such as alkaline phosphatase, horse radish peroxidase, α-galactosidase, and the like.

The term "general enrichment media" refers to any media which is known to be useful for facilitating the growth of microorganisms. Briefly, a variety of general enrichment media are commercially available and/or can be readily made, these include, but are not limited to, Tryptone based medium (e.g., Terrific Broth, SOB, SOC, and LB medium), NZCYM medium, minimal medium, lactose broth, buffered peptone water, Brain Heart Infusion medium, *Haemophilus* broth, Tryptic Soy broth, Nutrient broth and the like (see Sambrook et al., *Molecular Cloning: A Laboratory Manual*, 2$^{nd}$ ed., Cold Spring Harbor Press, 1989; Ausubel et al., *Current Protocols in Molecular Biology*, Greene Publishing, 1995; commercially available from Sigma Chemical Co, St. Louis, Mo. and Difco Laboratories Inc., Detroit, Mich.).

The present invention generally provides methods for detecting pathogens in a sample by culturing the sample at a first temperature that allows optimal growth of the pathogen while preventing expression of a particular protein or other pathogen product of interest (e.g., flagella or other cell protein that can be specifically detected using any of a variety of detection reagents/assays). The sample is then grown at a second temperature at which the previously inhibited protein is expressed. The sample is then subjected to any of a variety of detection assays for detecting the protein or product of interest. In this manner, the pathogen is detected in the sample.

Any of a variety of culture conditions known to the skilled artisan for the growth of pathogens can be used in the methods of the present invention, such as those described in *Current Protocols in Microbiology*, (Eds. R. Coico, T. Kowalik, J. Quarles, B. Stevenson, and R. Taylor; John Wiley & Sons, Inc, NY, N.Y. 2000-2006). The present invention uses any of several widely recognized general enrichment media such as tryptic soy broth, nutrient broth, buffered peptone water, lactose broth, brain heart infusion broth, or similar media.

As would be recognized by the skilled artisan, the first and second temperatures of the present methods will vary depending on the organism to be detected and the temperature-regulated protein or product of interest. As an illustration, *Listeria* grow at 37° C. and at 30° C. At 37° C., *Listeria* grow well but do not produce flagella while at 30° C., *Listeria* grow and also produce flagella. When allowed to grow at 37° C. for a period of time, this allows for enrichment of the bacteria in the sample. Once allowed to grow at 30° C. for a period of time, the enriched bacteria express flagella which can then be used to capture and detect the presence of the bacteria in the sample. Thus, the present method allows for the use of differential temperature for the growth of a pathogen, within the same container, to induce maximum possible growth levels and then transfer of the entire container to a second temperature to allow the production of the temperature-regulated protein. In this manner, the total assay time for detection of the pathogen is decreased and the sensitivity improved.

Accordingly, the first and second temperatures of the present invention may be any temperature appropriate for growth/inhibition of the protein of interest and growth/production of the protein of interest. For example, the first and second temperatures may range from 20° C.-40° C. In certain embodiments, the first temperature may be 20, 21, 22, 23, 24, 25, 26, 27, 28, 29, 30, 31, 32, 33, 34, 35, 36, 37, 38, 39, or 40° C. and the second temperature may be 20, 21, 22, 23, 24, 25, 26, 27, 28, 29, 30, 31, 32, 33, 34, 35, 36, 37, 38, 39, or 40° C.

The methods of the present invention can be used to detect any of a variety of pathogens including but not limited to *Listeria*, Enterohemorrhagic *E. coli* (EHEC), *Salmonella, Shigella, Campylobacter, Aeromonas hydrophilia, Aeromonas caviae, Aeromonas sobria, Streptococcus uberis, Enterococcus faecium, Enterococcus faecalis, Bacillus sphaericus, Pseudomonas fluorescens, Pseudomonas putida, Serratia liquefaciens, Lactococcus lactis, Xanthomonas maltophilia, Staphylococcus simulans, Staphylococcus hominis, Streptococcus constellatus, Streptococcus anginosus, Escherichia coli, Staphylococcus aureus, Mycobacterium fortuitum*, and *Klebsiella pneumonia*.

By "bacteria" is meant one or more viable bacteria existing or co-existing collectively in a test sample. The term may refer to a single bacterium (e.g., *Aeromonas hydrophilia, Aeromonas caviae, Aeromonas sobria, Streptococcus uberis, Enterococcus faecium, Enterococcus faecalis, Bacillus* sphaericus, Pseudomonas fluorescens, Pseudomonas putida, Serratia liquefaciens, Lactococcus lactis, Xanthomonas maltophilia, Staphylococcus simulans, Staphylococcus hominis, Streptococcus constellatus, Streptococcus anginosus, Escherichia coli, Staphylococcus aureus, Mycobacterium fortuitum, and Klebsiella pneumonia), a genus of bacteria (e.g., streptococci, pseudomonas and enterococci), a number of related species of bacteria (e.g., coliforms), an even larger group of bacteria having a common characteristic (e.g., all gram-negative bacteria), a group of bacteria commonly found in a food product, an animal or human subject, or an environmental source, or a combination of two or more bacteria listed above. The bacteria include those described or referred to in Bergey's Manual of Systematic Bacteriology, 1989, Williams and Wilkins, U.S.A., incorporated by reference herein.

By "sample" or "test sample" is meant a piece, fraction, aliquot, droplet, portion, fragment, volume, or tidbit taken from a food product such as ground beef or chicken, a human or animal test subject, a soil, water, air or other environmental source, or any other source whose bacterial concentration is to be measured. A test sample may be taken from a source using techniques known to one skilled in the art, including, but not limited to, those described or referred to in Compendium of Methods for the Microbiological Examination of Foods, Third Edition, Edited by Carl Vanderzant and Don F. Splittstoesser, Compiled by the APHA Technical Committee on Microbiological Methods for Foods, incorporated by reference herein.

As would be recognized by the skilled artisan, any protein whose expression is temperature-dependent may be useful in the methods of the present invention. The illustrative proteins described herein are bacterial flagella proteins but other temperature-regulated proteins are also contemplated herein.

In certain embodiments, the methods of detecting are specific for Listeria, Enterohemorrhagic E. coli (EHEC), Salmonella, or Campylobacter. In one embodiment, the method includes introducing the cultured sample into a detection system, such as a visual immunoprecipitate assay, an enzyme linked immunoassay, chemiluminescence, immunoblotting, or similar detection technology containing an antibody specific for the target protein or other product of a microorganism thereby producing a highly accurate result.

An additional aspect of the present invention is the use of a visual immunoprecipitate assay to detect the presence of a microorganism in a test sample. In the visual immunoprecipitate assay, the antibodies, including the "antibody-detection-reagent" initially located in the reagent zone, is typically either a polyclonal or monoclonal antibody. Further, when using a polyclonal antibody the antibody is preferably affinity column purified prior to its utilization the present invention. The production of such antibodies is well known in the art. (See, e.g., Antibodies: A Laboratory Manual, Harlow and Lane (eds.), Cold Spring Harbor Laboratory Press, 1988). Suitable affinity purified antibodies can also be procured from commercially available sources. For example, a polyclonal antisera specific for Salmonella is available from Kirkegaard and Perry Laboratories, Gaithersburg, Md. A preferred visual immunoprecipitate assay is that which is described by U.S. Pat. No. 5,658,747. Briefly, U.S. Pat. No. 5,658,747 utilizes a lateral flow diagnostic device which comprises a reagent zone containing an antibody-detection reagent and a detection zone located downstream of the reagent zone and comprising an immobile binding partner capable of specifically binding said complex between the target microorganism and the antibody detection reagent.

Polyclonal antibodies can be readily generated by one of ordinary skill in the art via immunization of a variety of warm-blooded animals such as horses, cows, goats, sheep, dogs, chickens, turkeys, rabbits, mice, or rats. Briefly, the target microorganism, or an antigen specifically associated with the target microorganism, is utilized to immunize the animal. The immunogenicity of the protein or peptide of interest may be increased through the use of an adjuvant such as Freund's complete or incomplete adjuvant or by coupling to another protein such as ovalbumin or keyhole limpet hemocyanin (KLH).

Monoclonal antibodies can also be readily generated using well-known techniques. (See, e.g., Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), supra.) Briefly, as one example, a subject animal is immunized as with the production of a polyclonal antibody. Alternatively, in vitro immunization techniques suitable for the production of monoclonal antibodies are also known in the art. Antibody-producing cells are then fused to immortal myeloma cells to provide an immortal hybridoma cell line. Following the fusion, the cells are placed into culture plates containing a suitable medium, traditionally HAT medium, although other suitable media are known in the art. After about seven days, the resulting fused cells or hybridomas may be screened in order to determine the presence of antibodies which recognize the desired antigen. Following several clonal dilutions and reassays, hybridoma producing antibodies that bind to the protein of interest can be isolated.

Other techniques can also be utilized to construct monoclonal antibodies or binding partners. (See, e.g., Huse et al., "Generation of a Large Combinational Library of the Immunoglobulin Repertoire in Phage Lambda," Science 246:1275-1281, 1989; Sastry et al., "Cloning of the Immunological Repertoire in Escherichia coli for Generation of Monoclonal Catalytic Antibodies: Construction of a Heavy Chain Variable Region-Specific cDNA Library," Proc. Natl. Acad. Sci. USA 86:5728-5732, 1989; Alting-Mees et al., "Monoclonal Antibody Expression Libraries: A Rapid Alternative to Hybridomas," Strategies in Molecular Biology 3:1-9, 1990; Larrick et al., "Polymerase Chain Reaction Using Mixed Primers: Cloning of Human Monoclonal Antibody Variable Region Genes From Single Hybridoma Cells," BioTechnology 7:934-938, 1989.)

Once a suitable antibody has been obtained, it may be isolated or purified by many techniques well known to those of ordinary skill in the art (see Antibodies: A Laboratory Manual, Harlow and Lane, supra).

Antibodies useful in the present invention are preferably capable of selectively detecting all of the strains of a target microorganism in the presence of numerous antigenically related organisms. Further, the antibodies are preferably capable of such detection with a low tolerance for non-specific binding (which leads to a false positive result) and a very low, preferably zero, failure to bind target the microorganism (which leads to a false negative result).

In certain embodiments, the sample is a solution containing, or consisting essentially of, an unpurified field sample such as a food, water, dirt, cosmetic, wastewater, industrial, pharmaceutical, botanical, environmental and other types of samples analyzed by enrichment-detection methods. Alternatively, the sample may be a biological fluid such as a body fluid. In a further embodiment, the sample may be partially or substantially purified prior to culturing the sample according to the methods of the present invention.

Following incubation of the sample under appropriate conditions including the first and second temperatures, the results are detected preferably using a rapid detection method such as, but not limited to, visual immunoprecipitate assay, enzyme linked immunoassay, chemiluminescence, immunoblotting, or similar detection technology. Such methodologies are described in greater detail in U.S. Pat. No. 5,658,747 and PCT WO 95/30903.

Another aspect of the present invention provides a method for detecting a microorganism in a test sample wherein the test sample is incubated in an appropriate medium and a first temperature for sufficient time to enrich levels of microorganisms followed by incubation in an appropriate medium and a second temperature suitable for production of a temperature-regulated detectable protein by the microorganism. Subsequently, the presence of pathogenic microorganisms is detected by utilizing immuno-based detection methodologies, which include but are not limited to, immuno-affinity, visual immunoprecipitation, enzyme linked immunoassay, chemiluminescence, immunoblotting, and the like. Alternatively, the exposure of antigen in a sample may be enhanced by treatment with detergent prior to or contemporaneously with detection. In a further alternative embodiment, the exposure of antigen in a sample may be enhanced by heating the sample in the presence of the detergent, prior to or contemporaneously with detection The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, U.S. Provisional Patent Application No. 60/837,469 filed Aug. 14, 2006 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for capturing *Listeria* in a sample comprising:
   (a) culturing the *Listeria* in the sample in a liquid general enrichment medium in a container at a first temperature wherein the first temperature is about 37° C. and prevents production of at least one endogenous protein and wherein the first temperature allows for optimal growth of the *Listeria*; then
   (b) transferring the entire container comprising the liquid general enrichment medium and the cultured *Listeria* of step (a) to a second temperature, wherein the second temperature is about 30° C.;
   (c) culturing the *Listeria* in the sample in the liquid general enrichment medium in the same container at the second temperature wherein the second temperature allows production of the at least one endogenous protein; and
   (d) contacting the cultured *Listeria* of step (c) with a reagent that specifically binds to the at least one endogenous protein;
   thereby capturing *Listeria* in the sample.

2. The method of claim 1, wherein the at least one endogenous protein comprises a flagellin protein.

3. A method for capturing *Listeria* in a sample comprising:
   (a) culturing the *Listeria* in the sample in a liquid general enrichment medium in a container at a first temperature wherein the first temperature is about 37° C. and prevents production of at least one endogenous protein and wherein the first temperature allows for optimal growth of the *Listeria*; then
   (b) transferring the entire container comprising at least a portion of the liquid general enrichment medium and the cultured *Listeria* of step (a) to a second temperature, wherein the second temperature is about 30° C.;
   (c) culturing the *Listeria* in the sample in the liquid general enrichment medium in the same container at the second temperature wherein the second temperature allows production of the at least one endogenous protein; and
   (d) contacting the cultured *Listeria* of step (c) with a reagent that specifically binds to the at least one endogenous protein;
   thereby capturing the *Listeria* in the sample.

* * * * *